US00PP35784P2

(12) United States Plant Patent
Mathey

(10) Patent No.: US PP35,784 P2
(45) Date of Patent: Apr. 30, 2024

(54) ***PHILADELPHUS* PLANT NAMED 'SMNPSDW'**

(50) Latin Name: *Philadelphus coronarius*
Varietal Denomination: SMNPSDW

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,898

(22) Filed: Aug. 30, 2023

(51) Int. Cl.
*A01H 5/02* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP25,303 P2 * 2/2015 Zampini ..... A01H 5/02 Plt./226

* cited by examiner

*Primary Examiner* — Karen M Redden
(74) *Attorney, Agent, or Firm* — C. Anne Whealy

(57) ABSTRACT

A new and distinct cultivar of *Philadelphus* plant named 'SMNPSDW', characterized by its upright to slightly outwardly spreading and uniformly mounding plant habit; moderately vigorous growth habit and moderate growth rate; freely branching habit; dense and bushy appearance; dark green-colored leaves; numerous double type white-colored flowers that are fragrant; and good garden performance.

2 Drawing Sheets

Figure 1:
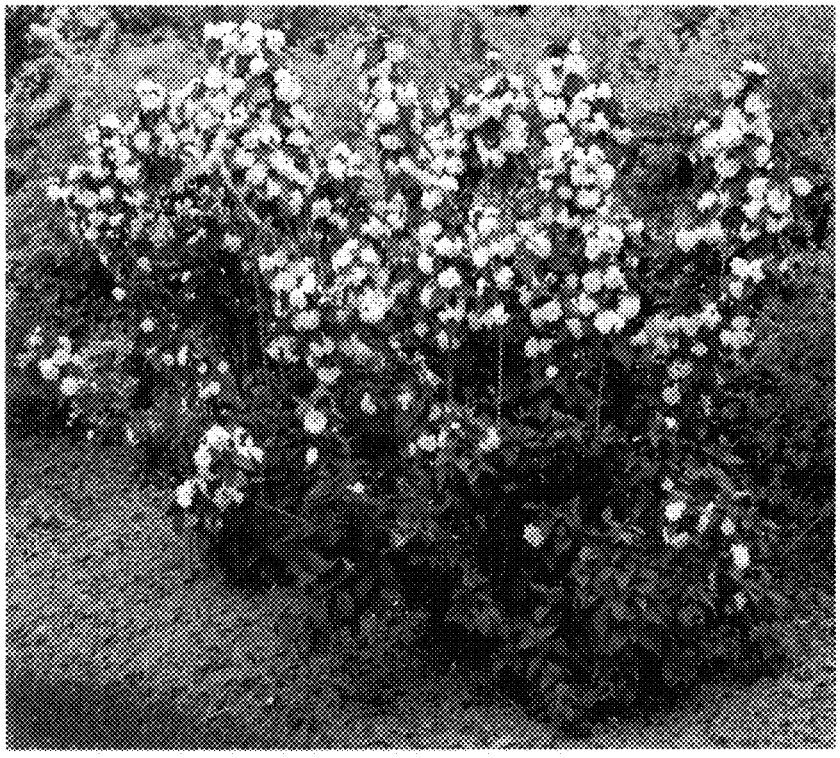

Botanical designation: *Philadelphus coronarius*.
Cultivar denomination: 'SMNPSDW'.

BACKGROUND OF THE INVENTION

The present invention relates to a new and distinct cultivar of *Philadelphus* plant, botanically known as *Philadelphus coronarius*, commonly referred to as Sweet Mock Orange and hereinafter referred to by the cultivar name 'SMNPSDW'.

The new *Philadelphus* is a product of a planned breeding program conducted by the Inventor in Grand Haven, Michigan. The objective of the breeding program was to develop new compact and freely flowering *Philadelphus* plants with double flowers.

The new *Philadelphus* plant originated from an open-pollination in 2015 in Grand Haven, Michigan of an unnamed proprietary selection of *Philadelphus coronarius*, not patented, as the female, or seed, parent with an unknown selection of *Philadelphus coronarius* as the male, or pollen, parent. The new *Philadelphus* plant was discovered and selected by the Inventor in 2016 as a single flowering plant within the progeny of the stated open-pollination in a controlled environment in Grand Haven, Michigan.

Asexual reproduction of the new *Philadelphus* plant by softwood stein cuttings in a controlled greenhouse environment in Grand Haven, Michigan since 2016 has shown that the unique features of this new *Philadelphus* plant are stable and reproduced true to type in successive generations of asexual reproduction.

SUMMARY OF THE INVENTION

Plants of the new *Philadelphus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNPSDW'. These characteristics in combination distinguish 'SMNPSDW' as a new and distinct *Philadelphus* plant:

1. Upright to slightly outwardly spreading and uniformly mounding plant habit.
2. Moderately vigorous growth habit and moderate growth rate.
3. Freely branching habit; dense and bushy appearance.
4. Dark green-colored leaves.
5. Numerous double type white-colored flowers that are fragrant.
6. Good garden performance.

Plants of the new *Philadelphus* can be compared to plants of the female parent selection. In side-by-side comparisons, plants of the new *Philadelphus* are more uniform than plants of the female parent selection.

Plants of the new *Philadelphus* can also be compared to plants of *Philadelphus* sp. 'Buckley's Quill', not patented. In side-by-side comparisons, plants of the new *Philadelphus* differ primarily from plants of 'Buckley's Quill' in the following characteristics:

1. Plants of the new *Philadelphus* have smaller flowers than plants of 'Buckley's Quill'.
2. Flowers of plants of the new *Philadelphus* have more petaloids than flowers of plants of 'Buckley's Quill'.
3. Flowers of plants of the new *Philadelphus* are denser and not as open as flowers of plants of 'Buckley's Quill'.

BRIEF DESCRIPTION OF THE PHOTOGRAPHS

The accompanying colored photographs illustrate the overall appearance of the new *Philadelphus* plant showing the colors as true as it is reasonably possible to obtain in colored reproductions of this type. Colors in the photographs may differ slightly from the color values cited in the detailed botanical description which accurately describe the colors of the new *Philadelphus* plant.

The photograph on the first sheet (FIG. 1) is a side perspective view of a typical flowering plant of 'SMNPSDW' grown in an outdoor nursery.

Figure 2:
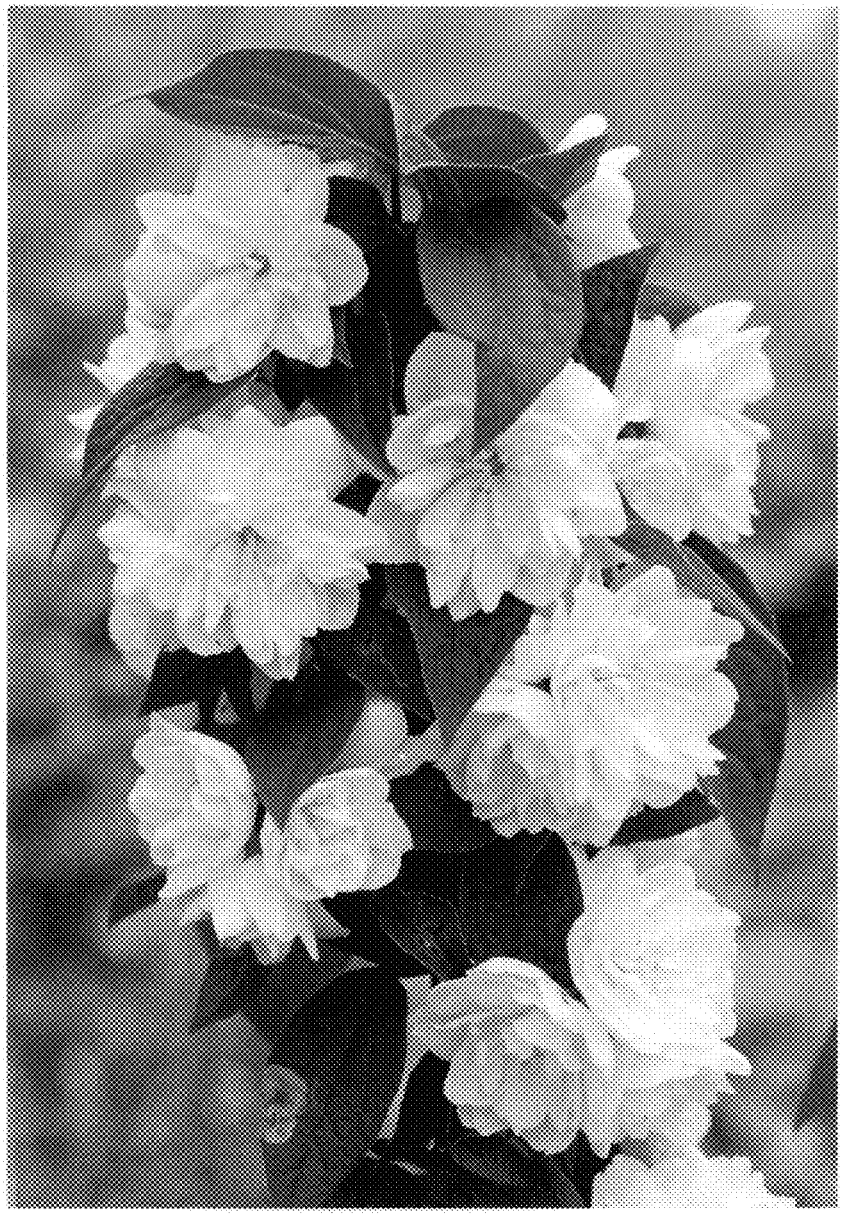

The photograph on the second sheet (FIG. 2) is close-up view of a typical flowering stein of 'SMNPSDW'.

DETAILED BOTANICAL DESCRIPTION

The following observations, measurements and values describe plants grown in the late spring in three-gallon containers in a polypropylene-covered shadehouse in Grand Haven, Michigan and under cultural practices typical of commercial *Philadelphus* production. During the production of the plants, day temperatures ranged from 18C to 27C and night temperatures ranged from 5C to 10C. Plants were five years old when the photographs were taken and three years old when the description was taken. In the description, color references are made to The Royal Horticultural Society Colour Chart, 2015 Edition, except where general terms of ordinary dictionary significance are used.

Botanical classification: *Philadelphus coronarius* 'SMNPSDW'.

Parentage:

*Female, or seed, parent.*—Unnamed proprietary selection of *Philadelphus coronarius*, not patented.

*Male, or pollen, parent.*—Unknown selection of *Philadelphus coronarius*, not patented.

Propagation:

*Type.*—By softwood stein cuttings.

*Time to initiate roots, summer.*—About two weeks at temperatures about 18C to 27C.

*Time to produce a rooted young plant, summer.*—About two months at temperatures about 18C to 27C.

*Root description.*—Thick to fine; fibrous; typically white to brown in color, actual color of the roots is dependent on substrate composition, water quality, fertilizer, substrate temperature and physiological age of roots.

*Rooting habit.*—Freely branching; dense.

Plant description:

*Plant form and growth habit.*—Perennial deciduous shrub; upright to slightly outwardly spreading and uniformly mounding plant habit; moderately vigorous growth habit and moderate growth rate.

*Branching habit.*—Freely branching habit; about 10 to 15 lateral branches develop per plant; pinching isn't required, however, will enhance lateral branch development.

*Plant height.*—About 63 cm.

*Plant diameter* (*area of spread*).—About 52 cm.

Lateral branch description:

*Length.*—About 50 cm.

*Diameter.*—About 3 mm to 5 mm.

*Internode length.*—About 4.9 cm.

*Aspect.*—Erect to about 20 degrees from vertical.

*Strength.*—Strong, rigid.

*Texture.*—When developing, slightly pubescent; with development becoming smooth and glabrous and subsequently, woody.

*Color, developing.*—Close to 144A.

*Color, developed.*—Close to 144A; when woody, close to 199B.

Leaf description:

*Arrangement.*—Opposite, simple.

*Length.*—About 9 cm.

*Width.*—About 5.25 cm.

*Shape.*—Elliptic.

*Apex.*—Acuminate.

*Base.*—Obtuse to cuneate.

*Margin.*—Slightly serrulate.

*Texture, upper surface.*—Sightly pubescent; somewhat coarse.

*Texture, lower surface.*—Slightly pubescent; somewhat coarse with pronounced venation.

*Venation pattern.*—Pinnate.

*Color.*—Developing leaves, upper surface: Close to 137B. Developing leaves, lower surface: Close to 138A and 138B. Fully expanded leaves, upper surface: Close to NN137A; venation, close to 144B. Fully expanded leaves, lower surface: Close to 147C; venation, close to 144B.

*Petioles.*—Length: About 1 cm. Diameter: About 2 mm. Texture, upper and lower surfaces: Slightly pubescent. Color, upper and lower surfaces: Close to 144B.

Flower description:

*Flower appearance and arrangement.*—Rotate double type flowers arranged in clusters of three to five along the length of the lateral branches; flowers dense with uniformly arranged petals and petaloids; freely flowering habit with about 50 flowers and flower buds per lateral branch with numerous flowers developing per plant during the flowering season; flowers face upright to outwardly.

*Fragrance.*—Strongly fragrant; sweet and pleasant with orange and jasmine notes.

*Natural flowering season.*—Plants flower continuously from the late spring into the early summer in Michigan.

*Flower longevity.*—Individual flowers last about one week on the plant; flowers not persistent.

*Flower diameter.*—About 4.75 cm.

*Flower depth.*—About 2 cm.

*Flower buds.*—Length: About 5 mm. Diameter: About 5 mm. Shape: Ovoid. Color: Close to 143B.

*Petals.*—Quantity and arrangement: About 15 to 20 arranged in about two whorls. Length: About 2.5 cm. Width: About 1.5 cm. Shape: Elliptic. Apex: Obtuse. Base: Obtuse to cuneate. Margin: Entire. Texture, upper and lower surfaces: Smooth, glabrous; silky. Color: When opening, upper and lower surfaces: Close to NN155B. Fully opened, upper and lower surfaces: Close to NN155B.

*Petaloids.*—Quantity and arrangement: About 25 to 30 arranged in about two whorls. Length: About 2 cm. Width: About 7.5 mm. Shape: Narrowly elliptic to oblong. Apex: Acute. Base: Cuneate. Margin: Entire to slightly serrulate. Texture, upper and lower surfaces: Smooth, glabrous; silky. Color: When opening and fully opened, upper surface: Close to NN155B. When opening and fully opened, lower surface: Close to NN155B.

*Sepals.*—Quantity and arrangement: Four in a single whorl and fused at the base. Length: About 1 cm. Width: About 4 mm. Shape: Narrowly elliptic. Apex: Acuminate. Margin: Entire. Texture, upper surface: Smooth, glabrous. Texture, lower surface: Slightly pubescent. Color, upper and lower surfaces: Close to 144A.

*Peduncles.*—Length: About 7.5 mm. Diameter: About 1 mm. Aspect: About 45 degrees from the lateral branch axis. Strength: Strong; somewhat flexible. Texture: Smooth, glabrous. Color: Close to 144A.

*Reproductive organs.*—Stamens: Quantity per flower: Typically all stamens are transformed into petaloids, occasionally, a few malformed stamens may be present. Filament length: About 1 cm. Filament color: Close to NN155B. Anther length: About 2 mm. Anther shape: Oblong. Anther color: Close to 8A. Pollen amount: If present, scarce. Pollen color: Close to 8A. Pistils: Quantity per flower: Three, fused. Pistil length: About 1 cm. Stigma shape: Rounded. Stigma color: Close to 8C. Style length: About 1 cm. Style color: Close to 8D. Ovary color: Close to 8D.

*Fruits and seeds.*—To date, fruit and seed development have not been observed on plants of the new *Philadelphus*.

Garden performance: Plants of the new *Philadelphus* have been observed to have good garden performance and to tolerate temperatures ranging from −31C to 38C.

Pathogen & pest resistance: To date, plants of the new *Philadelphus* have not been shown to be resistant to pathogens and pests common to *Philadelphus* plants.

It is claimed:

1. A new and distinct *Philadelphus* plant named 'SMNPSDW' as illustrated and described.

* * * * *